(12) United States Patent
Rassat et al.

(10) Patent No.: US 11,752,317 B2
(45) Date of Patent: Sep. 12, 2023

(54) HEMOSTASIS VALVE ORIENTATION RELATIVE TO THE FLUID SPACE IN A INTRODUCER SHEATH

(71) Applicant: Medtronic, Inc., Minneapolis, MN (US)

(72) Inventors: Jay T. Rassat, Buffalo, MN (US); Stephen Howard, Forest Lake, MN (US); Megan L. Platner, Eden Prairie, MN (US); Kevin A. Knutsen, Ramsey, MN (US)

(73) Assignee: Medtronic, Inc., Minneapolis, MN (US)

( * ) Notice: Subject to any disclaimer, the term of this patent is extended or adjusted under 35 U.S.C. 154(b) by 227 days.

(21) Appl. No.: 16/781,203

(22) Filed: Feb. 4, 2020

(65) Prior Publication Data
US 2021/0236789 A1 Aug. 5, 2021

(51) Int. Cl.
*A61M 39/06* (2006.01)

(52) U.S. Cl.
CPC ....... *A61M 39/06* (2013.01); *A61M 2039/062* (2013.01); *A61M 2039/064* (2013.01); *A61M 2205/02* (2013.01)

(58) Field of Classification Search
CPC ............ A61M 39/06; A61M 2039/062; A61M 2039/064; A61M 2039/2426; F16K 15/14; F16K 15/1471; F16K 7/04; F16K 7/12; F16K 21/00; F16K 21/04; F16K 31/445
USPC .................................................... 604/167.04
See application file for complete search history.

(56) References Cited

U.S. PATENT DOCUMENTS

| | | | |
|---|---|---|---|
| 4,895,565 A | * | 1/1990 | Hillstead .......... A61M 39/0606 604/167.04 |
| 5,000,745 A | | 3/1991 | Guest et al. |
| 5,102,395 A | | 4/1992 | Cheer et al. |
| 5,125,903 A | | 6/1992 | McLaughlin et al. |
| 5,154,701 A | | 10/1992 | Cheer et al. |
| 5,176,652 A | | 1/1993 | Littrell |
| 5,242,413 A | | 9/1993 | Heiliger |
| 5,366,478 A | | 11/1994 | Brinkerhoff et al. |
| 5,538,505 A | | 7/1996 | Weinstein et al. |
| 5,643,227 A | | 7/1997 | Stevens |
| 5,935,122 A | | 8/1999 | Fourkas et al. |
| 6,086,570 A | | 7/2000 | Aboul-Hosn et al. |
| 6,197,016 B1 | | 3/2001 | Fourkas et al. |
| 6,221,057 B1 | | 4/2001 | Schwartz et al. |

(Continued)

FOREIGN PATENT DOCUMENTS

| | | |
|---|---|---|
| EP | 0369314 A2 | 5/1990 |
| WO | 2007030746 A1 | 3/2007 |
| WO | 2016183392 A1 | 11/2016 |

OTHER PUBLICATIONS

International Search Report and Written Opinion dated May 7, 2021, for corresponding International Application No. PCT/US2021/013030; International Filing Date: Jan. 12, 2021 consisting of 10-pages.

*Primary Examiner* — Bhisma Mehta
*Assistant Examiner* — Nidah Hussain
(74) *Attorney, Agent, or Firm* — Michael Best & Friedrich LLP (57) ABSTRACT

A hemostasis device includes a valve, the valve being sized and configured to be disposed entirely within a handle of a medical device, the valve including a rim, the rim being sized and configured to seal with a lumen of the handle of the medical device.

15 Claims, 10 Drawing Sheets

(56) References Cited

U.S. PATENT DOCUMENTS

| | | | |
|---|---|---|---|
| 6,276,661 B1 | 8/2001 | Laird | |
| 6,610,031 B1 | 8/2003 | Chin | |
| 6,981,966 B2 | 1/2006 | Green et al. | |
| 7,172,580 B2 | 2/2007 | Hruska et al. | |
| 7,241,276 B2 | 7/2007 | Argentine et al. | |
| 2005/0033239 A1* | 2/2005 | Argentine | A61M 39/0606 604/167.04 |
| 2005/0096605 A1 | 5/2005 | Green et al. | |
| 2005/0171479 A1 | 8/2005 | Hruska et al. | |
| 2007/0078395 A1 | 4/2007 | Valaie | |
| 2008/0157017 A1* | 7/2008 | Macatangay | A61M 39/0613 251/314 |
| 2009/0118681 A1 | 5/2009 | Molgaard-Nielsen | |
| 2013/0160866 A1* | 6/2013 | Zinn | F16K 17/18 137/15.18 |
| 2014/0343512 A1 | 11/2014 | Fischer et al. | |
| 2017/0165466 A1* | 6/2017 | Lorimer | A61M 39/0613 |
| 2018/0333150 A1 | 11/2018 | Bak-Boychuk et al. | |

* cited by examiner

HEMOSTASIS VALVE ORIENTATION RELATIVE TO THE FLUID SPACE IN A INTRODUCER SHEATH

CROSS-REFERENCE TO RELATED APPLICATION n/a

FIELD

The present technology is generally related to hemostasis valves for introducer sheaths.

BACKGROUND

Cardiovascular interventional devices introduced into a given arterial or venous vessel for a variety of purposes, such as cryogenic or radiofrequency ablation, as well as angiographic procedures, have been known for many years. Several techniques for introducing such catheters are available, for example, surgically opening a vein or artery with a needle, inserting a guide wire into the vein or artery through the lumen of the needle, withdrawing the needle, inserting over the guide wire a dilator located inside an associated hemostasis valve and sheath, removing the dilator, and inserting a catheter through the hemostasis valve and sheath into the blood vessel. In this process, care must be exercised to prevent introduction of air into the vessel and it is desirable to avoid leakage of blood out of the proximal end of the sheath. To avoid the risk of introducing air into the blood stream, modern introducers for the placement of such interventional devices employ various types of hemostasis valves. Such hemostasis valves are designed for use with more than one diameter of catheters and guide wires that can be introduced within and through the hemostasis valve and outer sheath for the purposes listed above. However, a risk remains that air may enter the catheter or sheath, and thus the blood vessel, even with current hemostasis valves.

SUMMARY

The techniques of this disclosure generally relate to hemostasis valves for steerable sheaths.

In one aspect, a hemostasis device includes a valve, the valve being sized and configured to be disposed entirely within a handle of medical device, the valve including a rim, the rim be sized and configured to seal with a lumen of the handle of the medical device.

In another aspect of this embodiment, the valve is a disk valve.

In another aspect of this embodiment, the valve includes a valve body, and wherein the valve body defines a first diameter and the rim defines a second diameter larger than the first diameter.

In another aspect of this embodiment, the medical device is an introducer sheath.

In another aspect of this embodiment, the valve includes a proximal portion configured to be proximate the proximal end of the handle and a distal portion configured to be disposed proximate the proximal end of the steerable sheath, and wherein is disposed about the distal portion.

In another aspect of this embodiment, the valve body has a distal most end, and wherein the rim is proximal to the distal most end and substantially orthogonal to the distal most end.

In another aspect of this embodiment, when the valve is disposed within the lumen of the handle, the distal most end extends into the lumen.

In another aspect of this embodiment, the rim is a gasket.

In another embodiment, a hemostasis device includes a valve defining a substantially hyperboloid shape.

In another aspect of this embodiment, the valve includes a first portion symmetric with a second portion, and wherein the valve first includes a plurality of struts connecting the first portion to the second portion.

In another aspect of this embodiment, the first portion includes a first end and a second end, the first end having a larger diameter than the proximal end, and the second portion includes a third end and a fourth end, the fourth end includes a larger diameter than then third end, and wherein the second end and the third end each define a plurality of slits.

In another aspect of this embodiment, the valve is unitary.

In another aspect of this embodiment, the valve is sized to be disposed within at least a portion of a handle for a steerable sheath.

In another embodiment, a hemostasis device includes a valve includes first substantially toroidal portion and an opposite second substantially toroidal portion.

In another aspect of this embodiment, the valve includes a flange disposed between the first substantially toroidal portion and the second substantially toroidal portion.

In another aspect of this embodiment, the first substantially toroidal portion includes a first gasket and the second substantially toroidal portion includes a second gasket.

In another aspect of this embodiment, the flange is disposed between the first gasket and the second gasket.

In another aspect of this embodiment, the valve is sized to be disposed within at least a portion of a handle for a steerable sheath.

In another aspect of this embodiment, the first gasket and the second gasket each define rings.

In another aspect of this embodiment, the valve is composed of at least one from the group consisting of polyurethane and silicone.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

Figure 1:
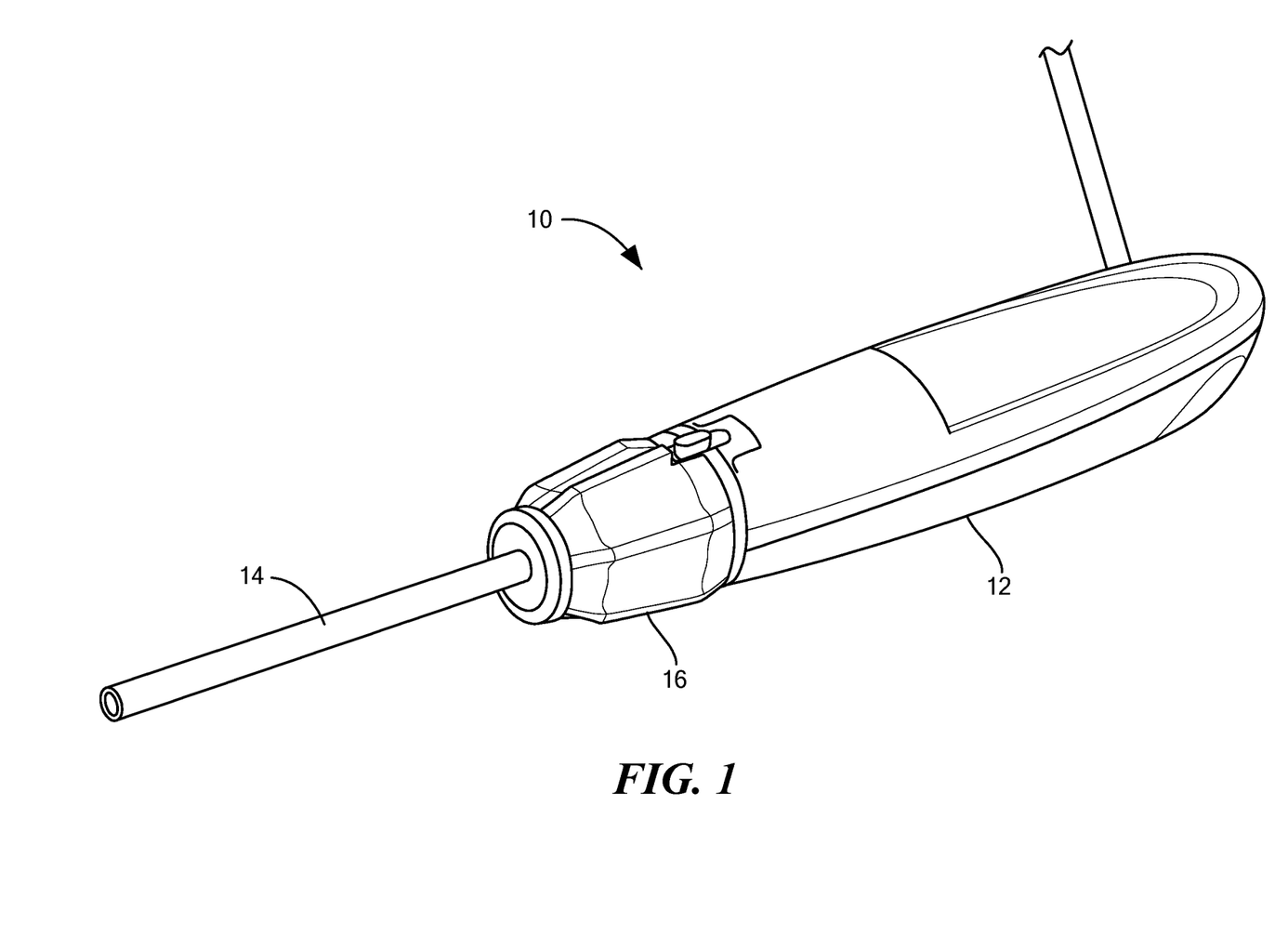
FIG. 1 is a perspective view of an exemplary steerable sheath in accordance with the principles of the present application.

Referring now to the drawings in which like reference designators refer to like elements, there is shown in FIG. 1 an exemplary medical device constructed in accordance with the principles of the present application and designated generally as "10." The medical device 10 may be a steerable sheath such as Medtronic's Flexcath® devices for use with cardiovascular interventions. In other configurations, the medical device 10 may be any medical device. In the configuration shown in FIG. 1, the medical device 10 includes a handle 12, a sheath 14 extending from the handle 12 and an actuator 16 configured to articulate the sheath 14 such that it can navigate the tortuous pathways of the vasculature.

Figure 2:
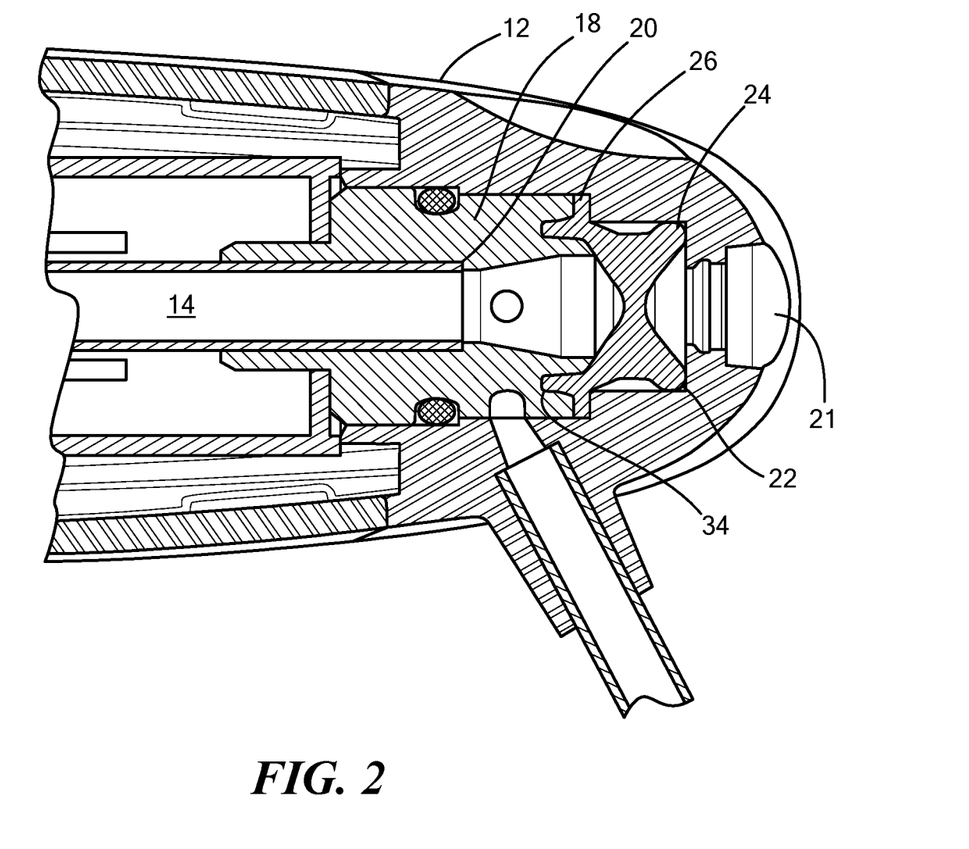
FIG. 2 is cross-sectional view of a proximal portion of the handle of the steerable sheath shown in FIG. 1.

Referring now to FIG. 2, the medical device 10 may further include lumen 18 in which a proximal end 20 of the sheath 14 is disposed. For example, the proximal end 20 of the sheath 14 may be disposed proximate an opening 21 within the handle 12 that allows another medical device, such as catheter (not shown) to be advanced into the handle 12 and into the sheath 14. To prevent air or other fluids such as blood from entering the sheath 14 during the inserting of the catheter, a hemostasis device 22 is at least partially disposed within the lumen 18 and entirely disposed within the handle 12. In an exemplary configuration, the hemostasis device 22 is valve 24 composed of, for example, a thermoplastic elastomer, silicone, or other rubbers. The handle 12 may provide a compressive force on the hemostasis device 22, for example, by a friction fit to provide for proper placement and function of the hemostasis device 22 such that air is not introduced into the introducer sheath 14.

Figure 3:
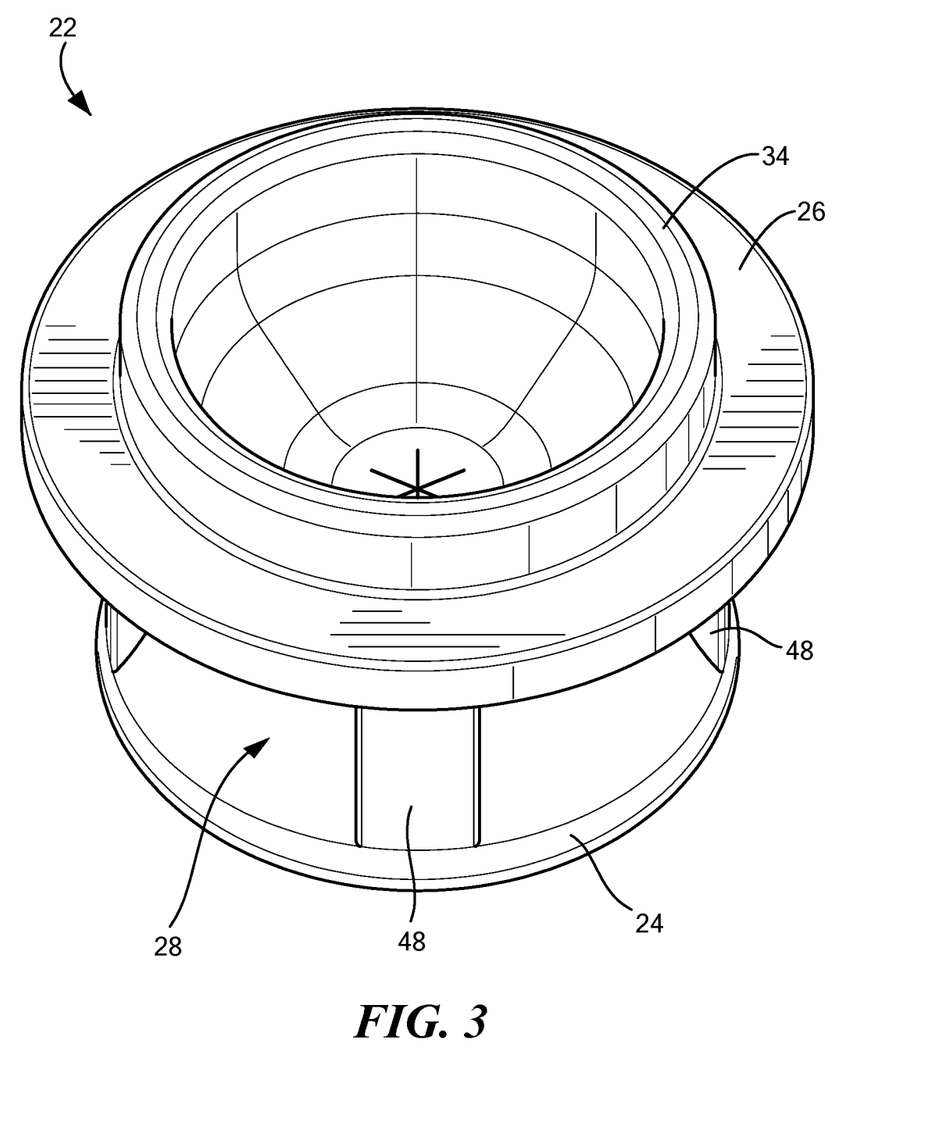
FIG. 3 is a perspective view of a hemostasis device constructed in accordance with the principles of the present application.
Figure 4:
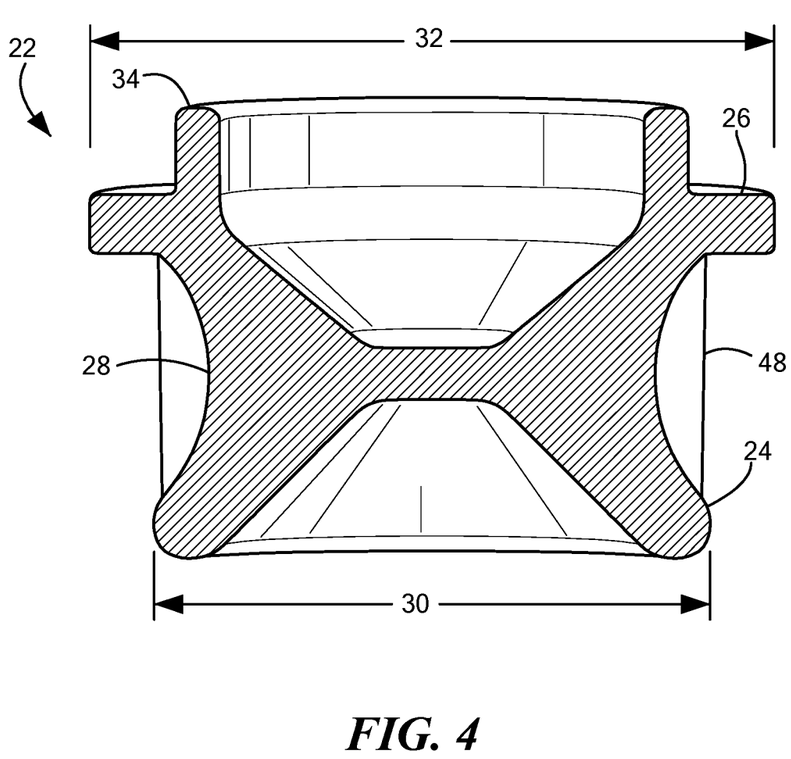
FIG. 4 is a cross-section view of the hemostasis device shown in FIG. 3.

Referring now to FIGS. 2-4, the valve 24 includes a rim 26 sized and configured to seal with the lumen 18 of the handle 14 of the medical device 12. For example, the valve 24 may include a valve body 28 which defines a first diameter 30. The rim 26 defines a second diameter 32 larger than the first diameter 30 and surrounds the valve body 28. In one configuration, the rim 26 is a gasket. In the configuration shown in FIG. 2, the rim 26 defines a perpendicular angle with the inner diameter of the lumen 18 and is substantially flush with the inner diameter of the lumen 18 when the valve 24 is disposed within the handle 12. In another configuration, the inner diameter of the lumen 18 is substantially co-planar with a distal most end 34 of the valve body 28. That is, the lumen 18 rest on the distal most end 34 of the valve body 28 and the rim is perpendicular to the distal most end 34 of the valve body 28. In an exemplary configuration, the valve body 28 is disposed proximate the opening 21 of the handle 12 and the rim 26 is disposed proximate the proximal end 20 of the sheath 14. This valve's 24 orientation within the sheath 14 prevents air from entering the sheath 14 and blood from leaking out of the sheath 14.

Figure 5:
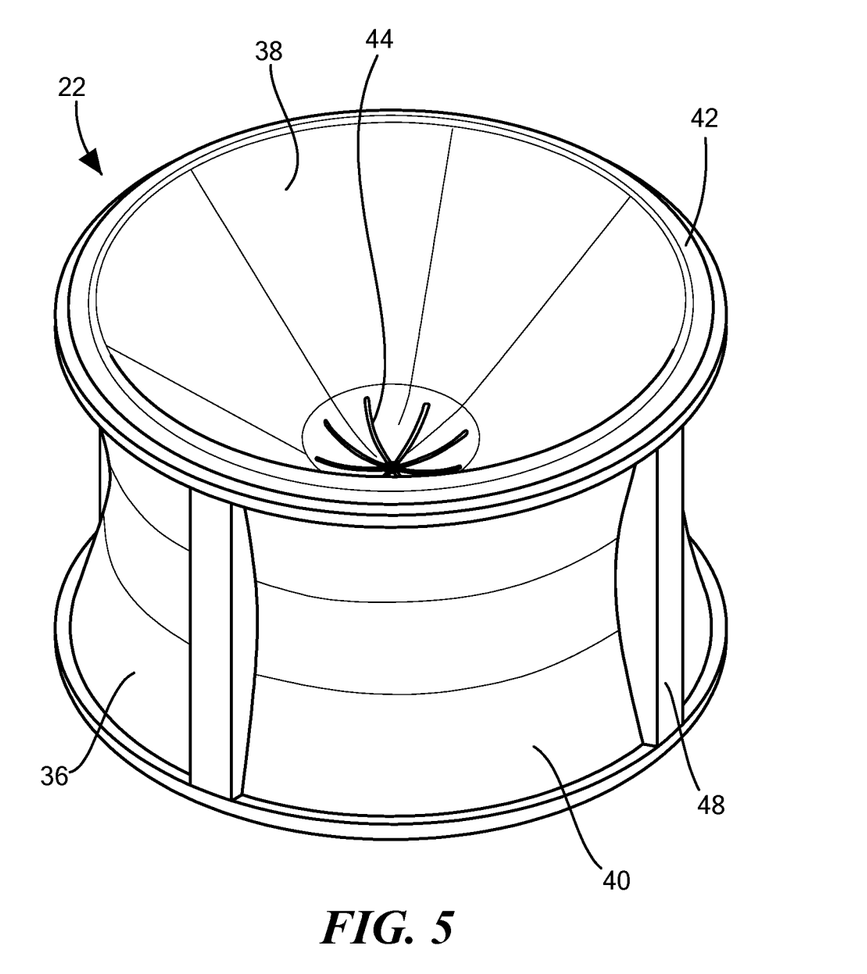
FIG. 5 is a perspective view of another hemostasis device constructed in accordance with the principles of the present application.
Figure 6:
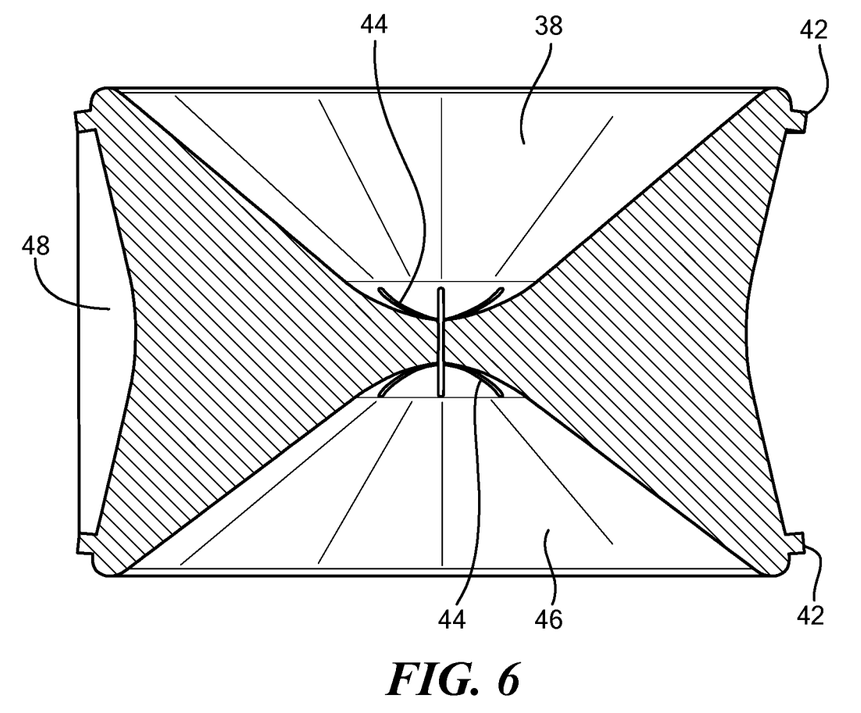
FIG. 6 is a cross-sectional view of the hemostasis device shown in FIG. 5.
Figure 7:
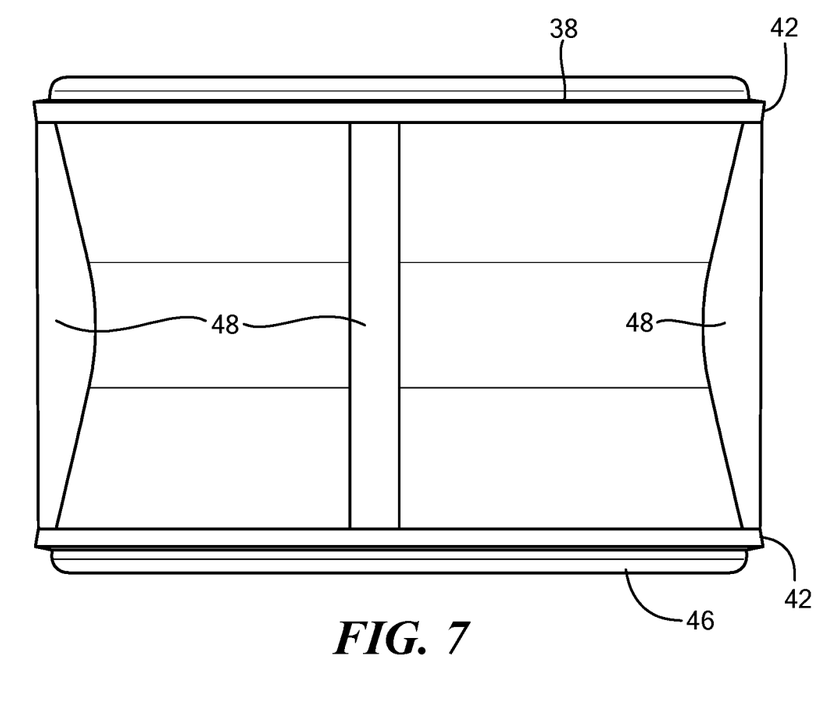
FIG. 7 is side view of the hemostasis device shown in FIG. 5.
Figure 8:
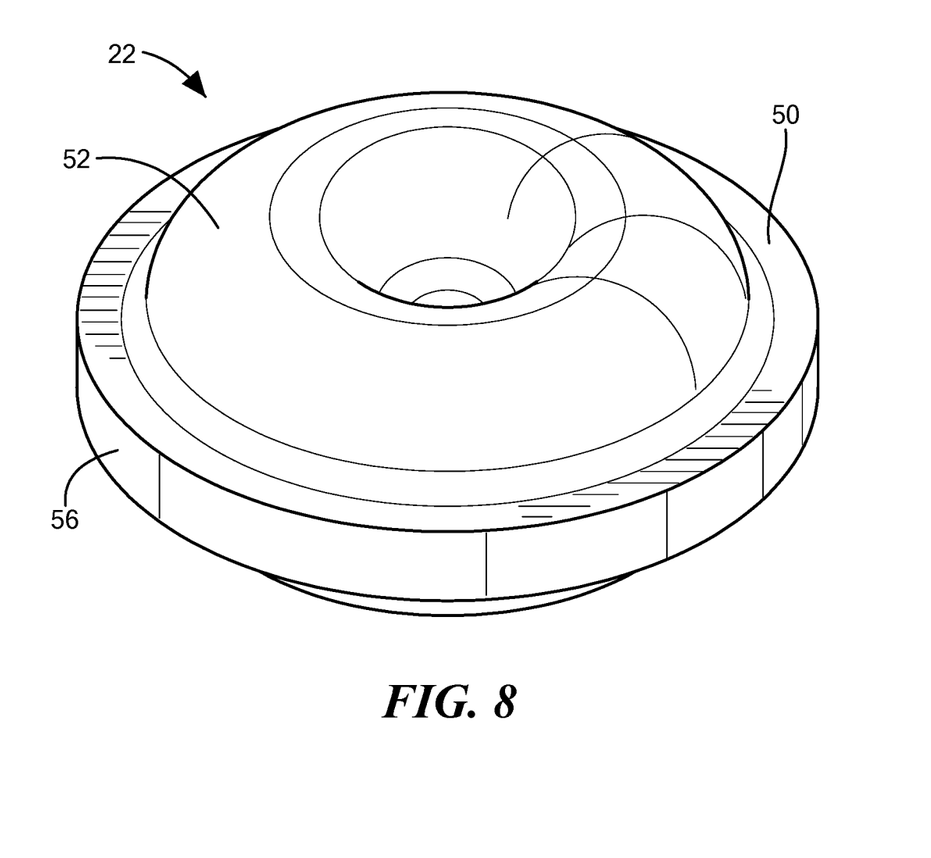
FIG. 8 is a perspective view of another hemostasis device constructed in accordance with the principles of the present application.
Figure 9:
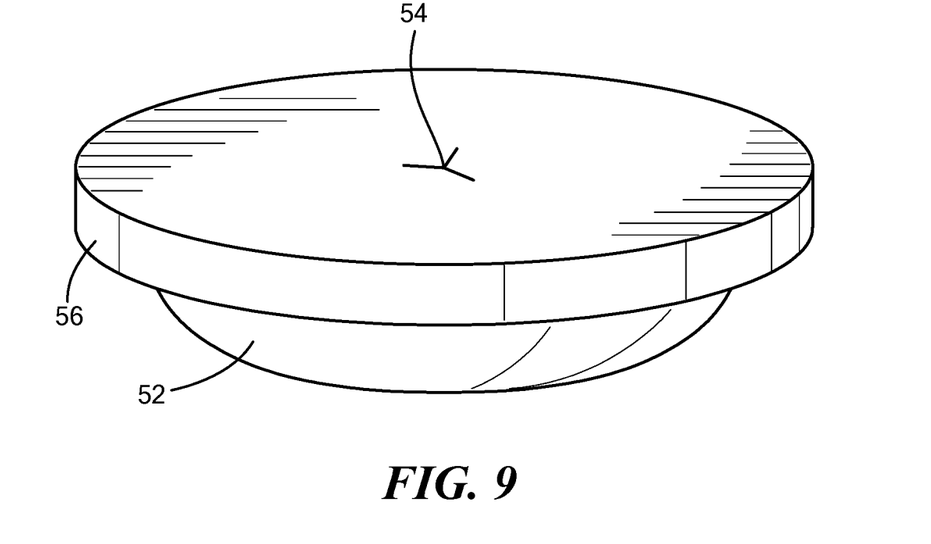
FIG. 9 is a view of a first portion of the hemostasis device shown in FIG. 8.
Figure 10:
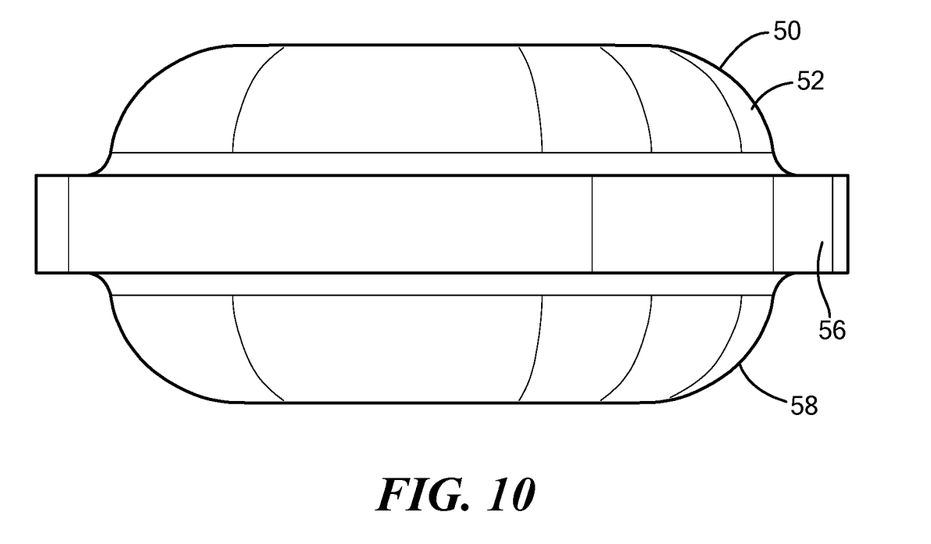
FIG. 10 is side view of the hemostasis device shown in FIG. 8.

Referring now to FIGS. 5-7, in another configuration, the hemostasis device 22 is valve 36. Valve 36 may be sized and configured to be entirely disposed within the handle 12 of device 10 and at least partially disposed within the lumen 18 of the handle 12. Valve 36 may be unitary valve defining a substantially hyperboloid shape, i.e. an hour-glass shape. As shown in FIG. 5, valve 36 may include a first portion 38, which may be conical or substantially conical, disposed within a valve body 40. The first portion 38 may include a rim 42 sized and configured to engage lumen 18 of device 10 as discussed above. The first portion 38 may further define a plurality of slits 44 at a distal end of the first portion to facilitate the introduction of a catheter or other device through the valve. The slits 44 may be tricuspid slits, or any other slit geometry configured to allow a device such a catheter to pass through. In another configuration, the valve 36 may include the first portion 38 symmetric with a second portion 46, which coupled together. The first portion 38 and the second portion 46 may each define the same or similar conical geometry and include respective slits 44 facing each other as shown in FIG. 7. Optionally, a plurality of struts 48 radially disposed about the valve 36 configured to provide longitudinal support to the first portion 38 and/or second portion 46, depending on the configuration. Any number of struts 48 may be included and they may extend into the interior of the valve 36. For example, as shown in FIGS. 6 and 7, the struts 48 extend toward the interior of the valve 36 and extend between the rim 42 of the first portion 38 and the rim 42 of the second portion 46.

Figure 11:
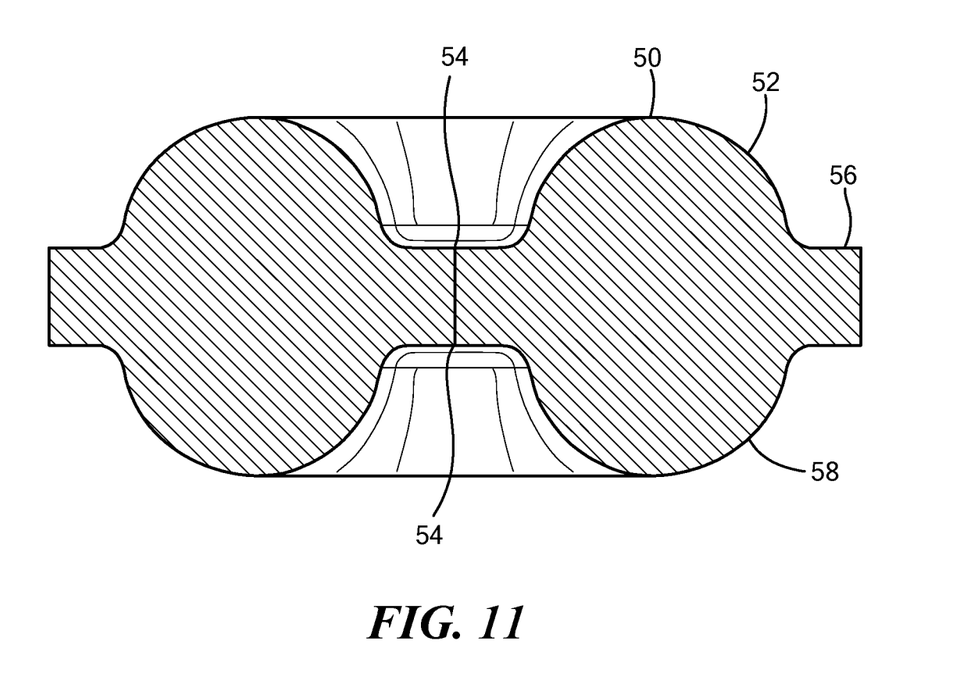
FIG. 11 is a cross-sectional view of the hemostasis device shown in FIG. 8.

Referring now to FIGS. 8-11, in another configuration, the hemostasis device 22 is a valve 50. Valve 50 may include a first substantially toroidal, or doughnut shaped, portion 52 defining a plurality of slits 54, for example, tricuspid slits, (shown in FIG. 9) for passage of a catheter or other medical device. The valve may include a rim 56 similar to the rims disclosed above configured to engage the lumen 18 of the of the device 10 as discussed above. The valve 50 may be unitary or it may include a second substantially toroidal portion 58 symmetric and opposite with the first substantially toroidal portion 52. The first substantially toroidal portion 52 and the second substantially toroidal portion 58 may each define the same or similar geometry and include respective slits 54 facing each other as shown in FIG. 11.

Figure 12:
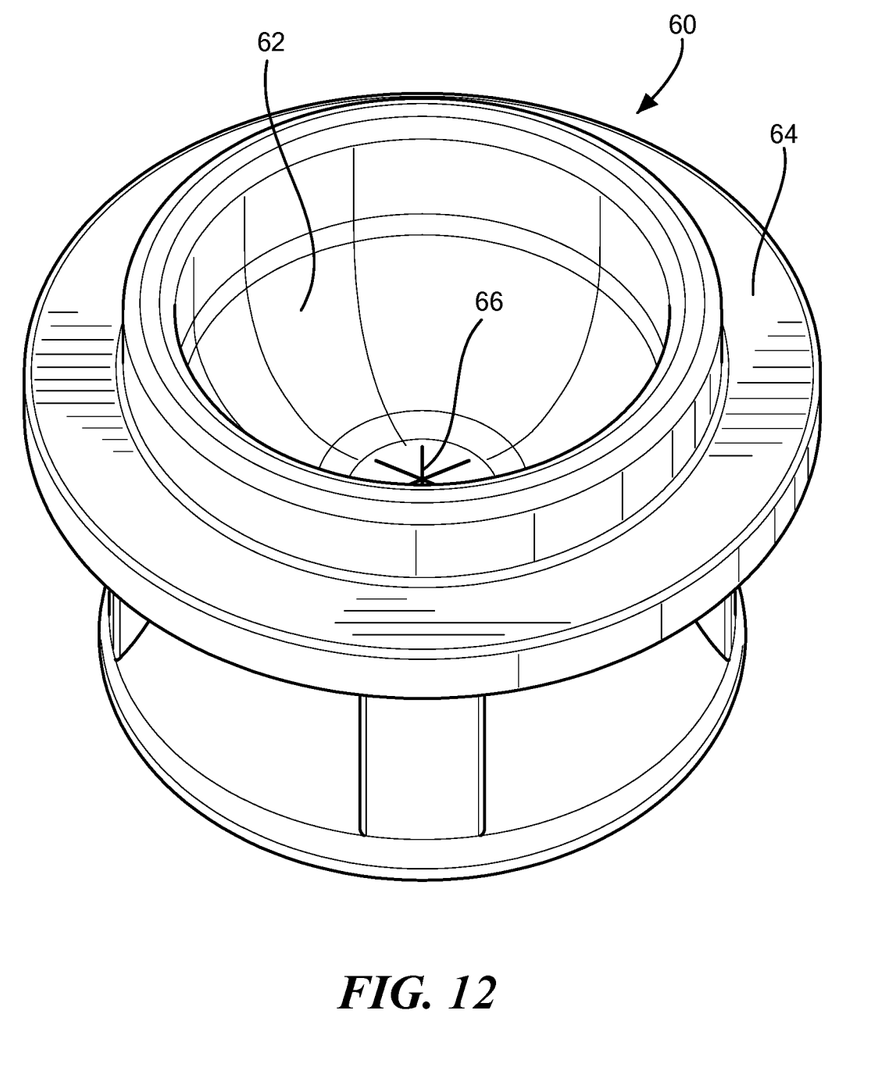
FIG. 12 is another embodiment of the hemostasis device shown in FIG. 3.
Figure 13:
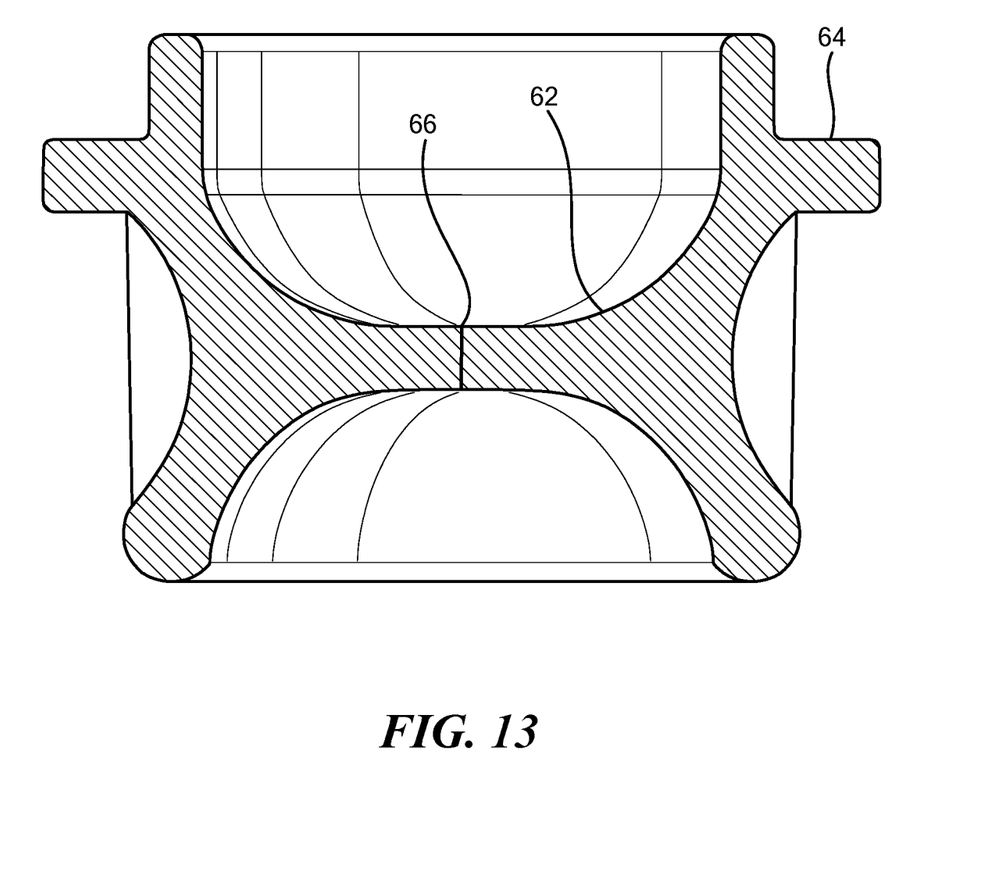
FIG. 13 is a cross-sectional view of the hemostasis device shown in FIG. 12.

Referring now to FIGS. 12-13, in another configuration of the valve 24 shown in FIG. 3, valve 60 may include a valve body 62, and further include a rim 64 sized and configured to seal with the lumen 18 of the handle 12 of the medical device 12. However, in this configuration, the valve body 64 tapers in a curved manner toward the slits 66, as opposed to a straight taper as shown in FIG. 4.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A hemostasis device, comprising:
a valve having a distal most end projecting axially outwardly, a rim located proximal the distal most end and projecting radially outwardly away from the distal most end, a first valve portion located proximal the rim, a second valve portion located proximal the first valve portion, a first plurality of slits, and a second plurality of slits, the valve being sized and configured to be disposed entirely within a handle of a medical device, the rim and the distal most end being sized and configured such that the rim is configured to seal with a lumen of the handle of the medical device, and the lumen is configured to rest on the distal most end of the valve, the first valve portion defining the first plurality of slits and the second valve portion defining the second plurality of slits, the first valve portion and the first plurality of slits being disposed opposite the second valve portion and the second plurality of slits,
wherein the first plurality of slits are defined on a curved, concave surface of the first valve portion, and wherein the second plurality of slits are defined on a curved, concave surface of the second valve portion.

2. The device of claim 1, wherein the valve is a disk valve.

3. The device of claim 1, wherein the valve includes a valve body, and wherein the valve body defines a first diameter and the rim defines a second diameter larger than the first diameter.

4. The device of claim 3, wherein the medical device is an introducer sheath.

5. The device of claim 4, wherein the handle has a proximal end and a distal end opposite the proximal end and the sheath has a proximal end and a distal end opposite the proximal end, the valve includes a proximal portion configured to be proximate the proximal end of the handle and a distal portion configured to be disposed proximate the proximal end of the sheath, and wherein the rim is disposed about the distal portion of the valve.

6. The device of claim 5, wherein the rim projects radially past both the first valve portion and the second valve portion.

7. The device of claim 6, wherein when the valve is disposed within the lumen of the handle, the distal most end extends into the lumen.

8. The device of claim 1, wherein the rim is a gasket.

9. The device of claim 1, wherein the valve is unitary.

10. The device of claim 1, further comprising the medical device having the handle with the lumen, wherein the rim is sealed to the lumen of the handle, and the lumen is resting on the distal most end of the valve.

11. A hemostasis device, comprising:
a valve defining a substantially hyperboloid shape extending about an axis, the valve having a first valve portion and a second valve portion opposite the first valve portion along the axis, the first valve portion defining a first plurality of slits and the second valve portion defining a second plurality of slits, the first plurality of slits being disposed directly and axially opposite the second plurality of slits,
wherein the first plurality of slits are defined on a curved, concave surface of the first valve portion, and wherein the second plurality of slits are defined on a curved, concave surface of the second valve portion.

12. The device of claim 11, wherein the first valve portion is symmetric with the second valve portion, and wherein the first valve portion includes a plurality of struts connecting the first valve portion to the second valve portion.

13. The device of claim 12, wherein the first valve portion includes a first end and a second end, the first end having a larger diameter than the second end, and the second valve portion includes a third end and a fourth end, the fourth end includes a larger diameter than the third end, and wherein the second end defines the first plurality of slits and the third end defines the second plurality of slits.

14. The device of claim 13, wherein the valve is unitary.

15. The device of claim 11, wherein the valve is sized to be disposed within at least a portion of a handle for a steerable sheath.

* * * * *